US012612582B2

(12) United States Patent
Nozaki et al.

(10) Patent No.: US 12,612,582 B2
(45) Date of Patent: Apr. 28, 2026

(54) CELL CULTURE SYSTEM

(71) Applicant: Hitachi, Ltd., Tokyo (JP)

(72) Inventors: Takayuki Nozaki, Tokyo (JP); Kunio Ohyama, Tokyo (JP); Masaharu Kiyama, Tokyo (JP); Kakuro Hirai, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 856 days.

(21) Appl. No.: 17/721,233

(22) Filed: Apr. 14, 2022

(65) Prior Publication Data

US 2022/0340847 A1      Oct. 27, 2022

(30) Foreign Application Priority Data

Apr. 27, 2021     (JP) ................................. 2021-074835

(51) Int. Cl.
*C12M 3/00*          (2006.01)
*B01L 3/00*          (2006.01)
(Continued)

(52) U.S. Cl.
CPC ......... *C12M 21/08* (2013.01); *B01L 3/50273* (2013.01); *C12M 23/16* (2013.01); (Continued)

(58) Field of Classification Search
None
See application file for complete search history.

(56) References Cited

U.S. PATENT DOCUMENTS

2005/0158701 A1*  7/2005  West ....................... G05D 21/02
                                                      435/286.1
2013/0143307 A1    6/2013  Nozaki et al.
(Continued)

FOREIGN PATENT DOCUMENTS

CN          103068962 A      4/2013
JP          2007312668 A    12/2007
                (Continued)

OTHER PUBLICATIONS

Document titled Cell Culturing Device, Culturing Vessel, and Holding Vessel, machine translation of WO 2014155500 A1 provided by Clarivate (Year: 2014).*

(Continued)

*Primary Examiner* — Holly Kipouros
(74) *Attorney, Agent, or Firm* — PROCOPIO, CORY, HARGREAVES & SAVITCH LLP

(57)          ABSTRACT

The present invention relates to an automatic culture device using a single-use closed system flow path for culturing a cell or a tissue, and realizes reduction in manufacturing cost and high integration property of a device. A cell culture system including an automatic culture device and an information processing device. The automatic culture device includes a plurality of types of closed system flow paths possible to be installed and removed, and a plurality of culture devices. The information processing device includes: an input device configured to receive, as an input, at least one piece of data selected from a group consisting of data of an identifier of a patient, data related to a transplantation method, data related to a type of cell, data related to the required number of cells, and data related to a treatment plan; an arithmetic device configured to select, based on the input data, from options of a cell culture method, the culture devices, and the closed system flow paths, the cell culture method, the culture device, and the closed system flow path to be used; and an output device configured to output a number of the closed system flow path to be used and a number of the culture device to be used.

4 Claims, 14 Drawing Sheets

(51) Int. Cl.

| | |
|---|---|
| *C12M 1/00* | (2006.01) |
| *C12M 1/34* | (2006.01) |
| *C12M 1/36* | (2006.01) |
| *C12M 3/06* | (2006.01) |
| *C12N 5/071* | (2010.01) |

(52) U.S. Cl.

CPC ............ *C12M 23/44* (2013.01); *C12M 27/18* (2013.01); *C12M 29/24* (2013.01); *C12M 41/34* (2013.01); *C12M 41/48* (2013.01); *C12N 5/0602* (2013.01); *B01L 2300/0829* (2013.01); *B01L 2300/0858* (2013.01); *B01L 2300/10* (2013.01)

(56) References Cited

U.S. PATENT DOCUMENTS

| | | |
|---|---|---|
| 2016/0319233 A1 | 11/2016 | Shimase et al. |
| 2017/0342365 A1* | 11/2017 | Nozaki .................. C12M 23/58 |

| | | |
|---|---|---|
| 2019/0010436 A1 | 1/2019 | Tsumura et al. |
| 2019/0330584 A1 | 10/2019 | Rathbone et al. |
| 2021/0115382 A1 | 4/2021 | Murthy et al. |

FOREIGN PATENT DOCUMENTS

| | | | | |
|---|---|---|---|---|
| JP | 2010-124703 A | 6/2010 | | |
| JP | 2017-121220 A | 7/2017 | | |
| JP | 2018-050550 A | 4/2018 | | |
| JP | 2020-124172 A | 8/2020 | | |
| SG | 146546 A1 * | 10/2008 | ............ | C12M 37/00 |
| WO | 2012/020458 A1 | 2/2012 | | |
| WO | WO-2014155500 A1 * | 10/2014 | ............ | C12M 23/48 |
| WO | WO-2021011547 A1 * | 1/2021 | ............ | G16H 10/40 |

OTHER PUBLICATIONS

He, Dong, "Project-based tutorial of RFID Technical application", Fudan University Press, http://www.fudanpress.com, (2021), in 8 pages, with English translation.

* cited by examiner

*FIG. 7A*            *FIG. 7B*
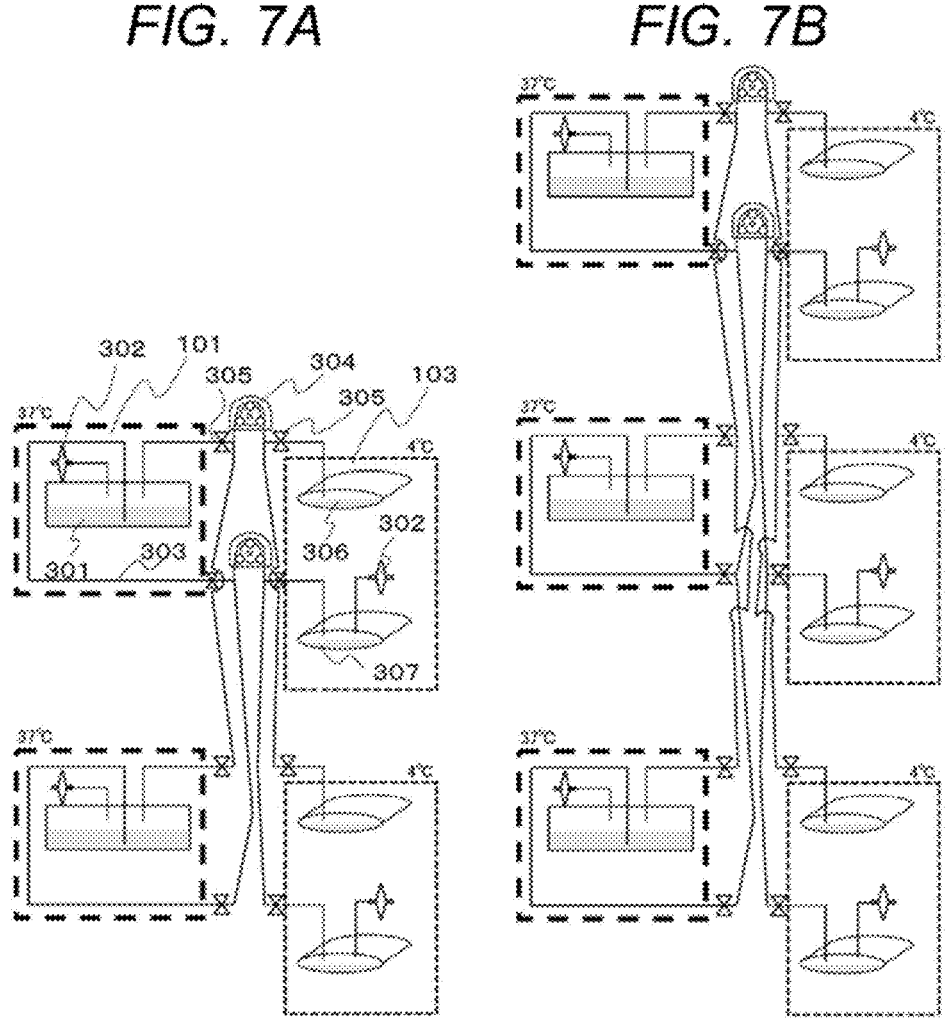

*FIG. 7C*            *FIG. 7D*
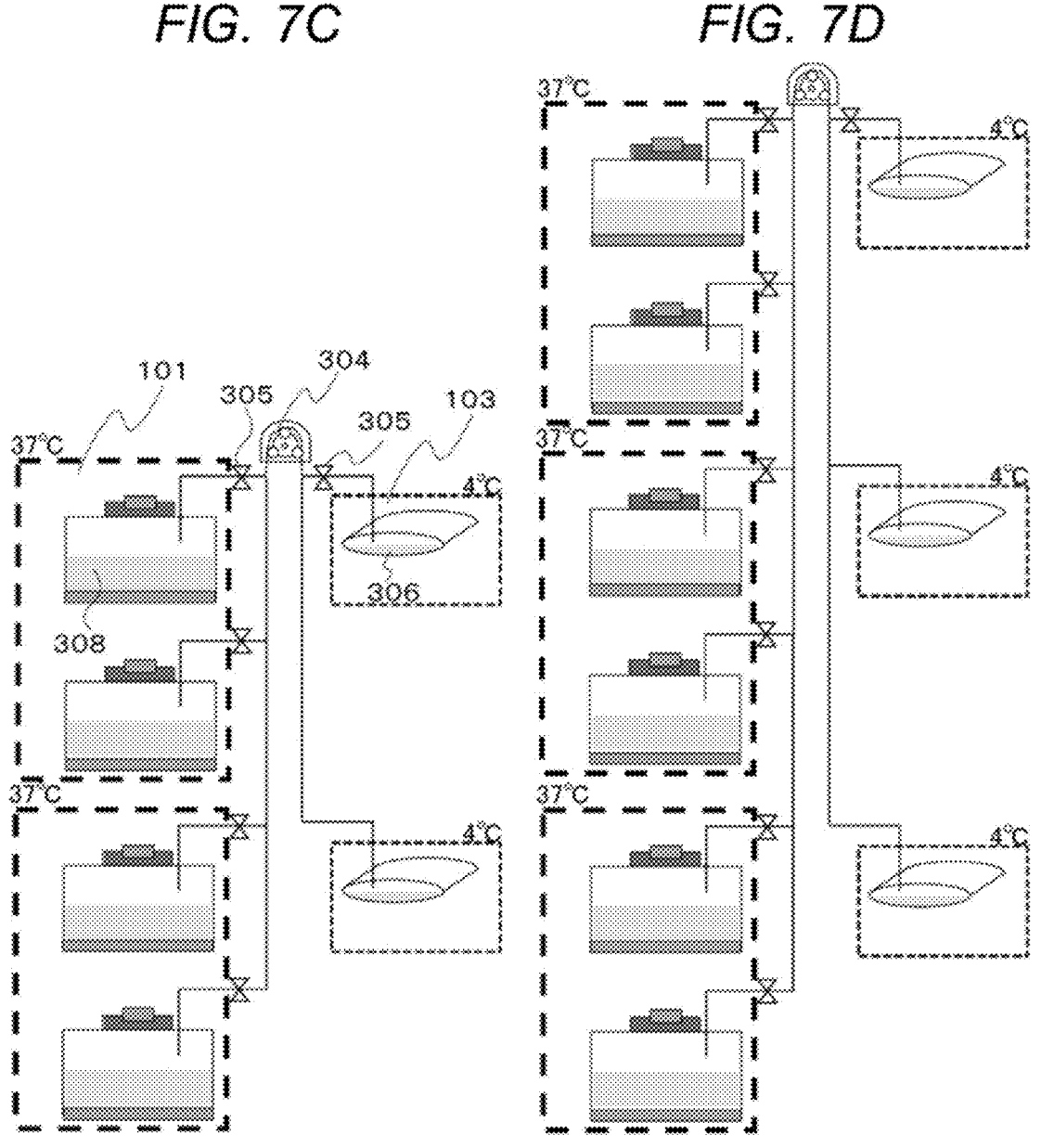

FIG. 8

| No. | PROCESS | MOTION OF INFORMATION | |
| --- | --- | --- | --- |
| | | INFORMATION EXTRACTED FROM DB | NEWLY GENERATED INFORMATION |
| 1 | PATIENT REGISTRATION | ― | <1> PATIENT ID <br> <2> BASIC PATIENT DATA SUCH AS PATIENT NAME, AGE, SEX, MEDICAL HISTORY, ETC. |
| 2 | TREATMENT METHOD DETERMINATION | <1> PATIENT ID <br> <2> PATIENT BASIC DATA | <3> TREATMENT METHOD BASED ON REGENERATIVE MEDICINE <br> <4> TYPE OF CELL <br> <5> REQUIRED NUMBER OF CELLS <br> <6> TRANSPLANTATION FORM <br> <7> TREATMENT SCHEDULE |
| 3 | MANUFACTURING METHOD DETERMINATION ① CULTURE CONTAINER | <1> PATIENT ID <4> TYPE OF CELL <br> <5> REQUIRED NUMBER OF CELLS <br> <6> TRANSPLANTATION FORM | <8> CULTURE METHOD <br> <9> TYPE OF CULTURE CONTAINER <br> <10> NUMBER OF CULTURE CONTAINERS |
| 4 | MANUFACTURING METHOD DETERMINATION ② FLOW PATH TO BE USED | <1> PATIENT ID <8> CULTURE METHOD <br> <9> TYPE OF CULTURE CONTAINER <br> <10> NUMBER OF CULTURE CONTAINERS | <11> TYPE OF CLOSED SYSTEM FLOW PATH TO BE USED <br> <12> LOT NUMBER OF CLOSED SYSTEM FLOW PATH TO BE USED |
| 5 | MANUFACTURING METHOD DETERMINATION ③ ACES TO BE USED | <1> PATIENT ID <br> <7> TREATMENT SCHEDULE <br> <11> TYPE OF CLOSED SYSTEM FLOW PATH TO BE USED | <13> NUMBER OF ACES TO BE USED <br> <14> DEVICE NUMBER OF ACES TO BE USED |
| 6 | CARRYING-OUT OF CLOSED SYSTEM FLOW PATH FROM WAREHOUSE | <1> PATIENT ID <br> <11> TYPE OF CLOSED SYSTEM FLOW PATH TO BE USED <br> <12> LOT NUMBER OF CLOSED SYSTEM FLOW PATH TO BE USED | <15> WORK PROCEDURE MANUAL RELATED TO CARRYING-OUT OF CLOSED SYSTEM FLOW PATH, DESCRIBING TYPE OF CLOSED SYSTEM FLOW PATH TO BE USED AND LOT NUMBER OF CLOSED SYSTEM FLOW PATH TO BE USED |
| 7 | ATTACHMENT OF CLOSED SYSTEM FLOW PATH TO ACES IN CELL PREPARATION CHAMBER | <1> PATIENT ID <br> <13> NUMBER OF ACES TO BE USED <br> <14> DEVICE NUMBER OF ACES TO BE USED | <16> WORK PROCEDURE MANUAL RELATED TO INSTALLATION OF CLOSED SYSTEM FLOW PATH TO ACES, DESCRIBING NUMBER OF ACES TO BE USED AND DEVICE NUMBER |
| 8 | EVALUATION OF CELL AFTER CULTURE | <1> PATIENT ID | <17> EVALUATION DATA SUCH AS NUMBER OF CELLS AFTER CULTURE AND SURVIVAL RATE IN EACH USED CULTURE CONTAINER |
| 9 | DETERMINATION OF IMPLEMENTATION FEASIBILITY OF TREATMENT METHOD BY REGENERATIVE MEDICINE | <1> PATIENT ID <3> TREATMENT METHOD BASED ON REGENERATIVE MEDICINE <4> TYPE OF CELL <br> <5> REQUIRED NUMBER OF CELLS <br> <6> TRANSPLANTATION FORM <br> <7> TREATMENT SCHEDULE <17> EVALUATION DATA | <18> DETERMINATION RESULT OF TRANSPLANTATION FEASIBILITY |

*FIG. 9*

CELL CULTURE SYSTEM

BACKGROUND OF THE INVENTION

1. Field of the Invention

The present invention relates to a cell culture system.

2. Description of the Related Art

Regenerative medicine, which recovers a function of an organ or the like by using a regenerated tissue or the like manufactured using cells as a material, is expected as a radical treatment for diseases for which there has been no treatment method from the past. Clinical applications for various tissues to be treated such as skin, cornea, esophagus, heart, bone, and cartilage are rapidly increasing. In a manufacturing process of the regenerated tissue, a stem cell is isolated from a biological sample collected from a patient or another person, and the isolated stem cell is proliferated or organized. The process is performed in a cell processing facility (CPF) in accordance with a standard operating procedure (SOP) satisfying a good manufacturing practice (GMP) that is a standard for manufacturing management and quality management of pharmaceuticals and the like.

The operation of the CPF requires large cost and personnel having a specialized culture technique. In addition, since the manufacturing process of the regenerated tissue is mainly performed by manual work, there is a limit in a manufacture amount of the regenerated tissue. Popularization of the regenerative medicine has been hindered by low productivity and high manufacturing cost, and automation of culture work particularly requiring labor and cost in the manufacturing process is expected. With the automation, it is possible to realize labor saving and cost reduction in the manufacturing of the regenerated tissue and mass production of the regenerated tissue.

Products that have already been marketed and products that are being developed include more regenerated tissues for an autologous transplantation than those for a heterologous transplantation. Since the autologous transplantation using a patient's own cells has a low possibility of rejection, a good treatment result is expected, and it is considered that a need of the autologous transplantation is huge from a viewpoint of improving QOL of the patient. In the autologous transplantation, since a regenerated tissue is manufactured on a basis of one patient, various types of regenerated tissues can be manufactured in small amounts. At this time, assuming manufacturing by an automatic culture device, it is preferable to perform the manufacturing for one patient by one automatic culture device in order to avoid a risk of biological contamination. On the other hand, assuming manufacturing of cells of a plurality of patients, it is also important that the automatic culture device is small in size and has high integration property. Therefore, it is important that the automatic culture device for the autologous transplantation is low in manufacturing cost and high in integration property.

The automatic culture device mainly includes two types, that is, an open system automatic culture device and a closed system automatic culture device. In the open system automatic culture device, an open system culture container such as a culture container and a culture plate of a type for opening and closing a lid, which is generally used in manual culture, is automatically handled in a closed space in which an articulated robot or the like is installed. The inside of the closed space can be decontaminated by a decontamination gas or the like. On the other hand, in the closed system automatic culture device, a closed system flow path having a closed space is automatically handled. The closed system flow path is in a state where a closed system culture container is constantly connected by a flow path tube or the like, and the inside of the closed system flow path is made aseptic by γ-ray sterilization or the like in advance.

When the open system automatic culture device and the closed system automatic culture device are compared, in the open system automatic culture device, the open system culture container is taken out from the open system automatic culture device after the regenerated tissue is manufactured, and the process proceeds to a next step, but there is a risk of biological contamination due to culture medium leakage or the like in transition of the open system culture container. In the closed system automatic culture device, although the closed system culture container is taken out from the closed system automatic culture device after the regenerated tissue is manufactured, and the process proceeds to a next step, since a culture medium leakage does not occur in transition of the closed system culture container, the risk of biological contamination is less likely to occur than in the open system automatic culture device using the open system culture container. The open system automatic culture device is often large because the articulated robot or the like is installed in the closed space. Therefore, when it is assumed that a plurality of open system automatic culture devices are used in an integrated state, a large-scale room of the CPF is required to store the open system automatic culture devices. The closed system automatic culture device can be miniaturized because only the inside of the closed system flow path is in an aseptic state. Therefore, it is easier to use a plurality of closed system automatic culture devices in an integrated state than the open system automatic culture devices.

As an example of the closed system automatic culture device, there is disclosed a device including a closed system culture container of one layer and in which a flow path for supplying or discharging a culture medium or the like is constantly connected (see JP-A-2007-312668). When supplying a culture medium or the like, a valve installed outside the closed system flow path is adjusted to operate a pump. The closed system flow path is used once in order to avoid the biological contamination. A plurality of devices may be used in an integrated state. There is also disclosed a closed system automatic culture device in which a plurality of types of flow paths, branches, and the like are provided in a closed system culture container (see US2019/0330584). In the device, by selecting an appropriate flow path or branch from the plurality of types of flow paths or branches, it is possible to execute an automatic culture protocol corresponding to the selected flow path or branch.

An object of the invention is to provide a novel cell culture system.

SUMMARY OF THE INVENTION

An aspect of the invention is a cell culture system including an automatic culture device and an information processing device. The automatic culture device includes a plurality of types of closed system flow paths possible to be installed and removed, and a plurality of culture devices. The information processing device includes: an input device configured to receive, as an input, at least one piece of data selected from a group consisting of data of an identifier of a patient, data related to a transplantation method, data related to a type of cell, data related to the required number of cells, and data related to a treatment plan; an arithmetic device configured to select, based on the input data, from options of a cell culture method, the culture devices, and the closed system flow paths, the cell culture method, the culture device, and the closed system flow path to be used; and an output device configured to output a number of the closed system flow path to be used and a number of the culture device to be used. The closed system flow path may include a valve for opening and closing a flow path tube, a pump for supplying a fluid or gas in the flow path tube, a culture medium container for holding a fresh culture medium, and a culture supernatant container for holding a fresh culture supernatant. One of the closed system flow paths may be provided for a plurality of the culture devices. The output device may output a work procedure protocol related to the closed system flow path to be used. The output device may output a work procedure protocol related to the selected culture device.

According to the automatic culture device according to the invention, for a plurality of culture devices, by using a culture program for operating the plurality of culture devices using a highly versatile closed system flow path, the integration property of the automatic culture device can be improved, and as a result, the manufacturing cost can be reduced.

BRIEF DESCRIPTION OF THE DRAWINGS

FIG. 7A is a diagram showing a closed system flow path installed in a plurality of culture devices according to the embodiment of the invention.

FIG. 7B is a diagram showing a closed system flow path installed in a plurality of culture devices according to the embodiment of the invention.

FIG. 7C is a diagram showing a closed system flow path installed in a plurality of culture devices according to the embodiment of the invention.

FIG. 7D is a diagram showing a closed system flow path installed in a plurality of culture devices according to the embodiment of the invention.

FIG. 8 is a diagram showing culture information related to a culture device to be used for culture and a closed system flow path according to the embodiment of the invention.

FIG. 9 is a diagram showing a flow of the culture information related to the culture device to be used for culture and the closed system flow path according to the embodiment of the invention.

DESCRIPTION OF THE PREFERRED EMBODIMENTS

Figure 1:
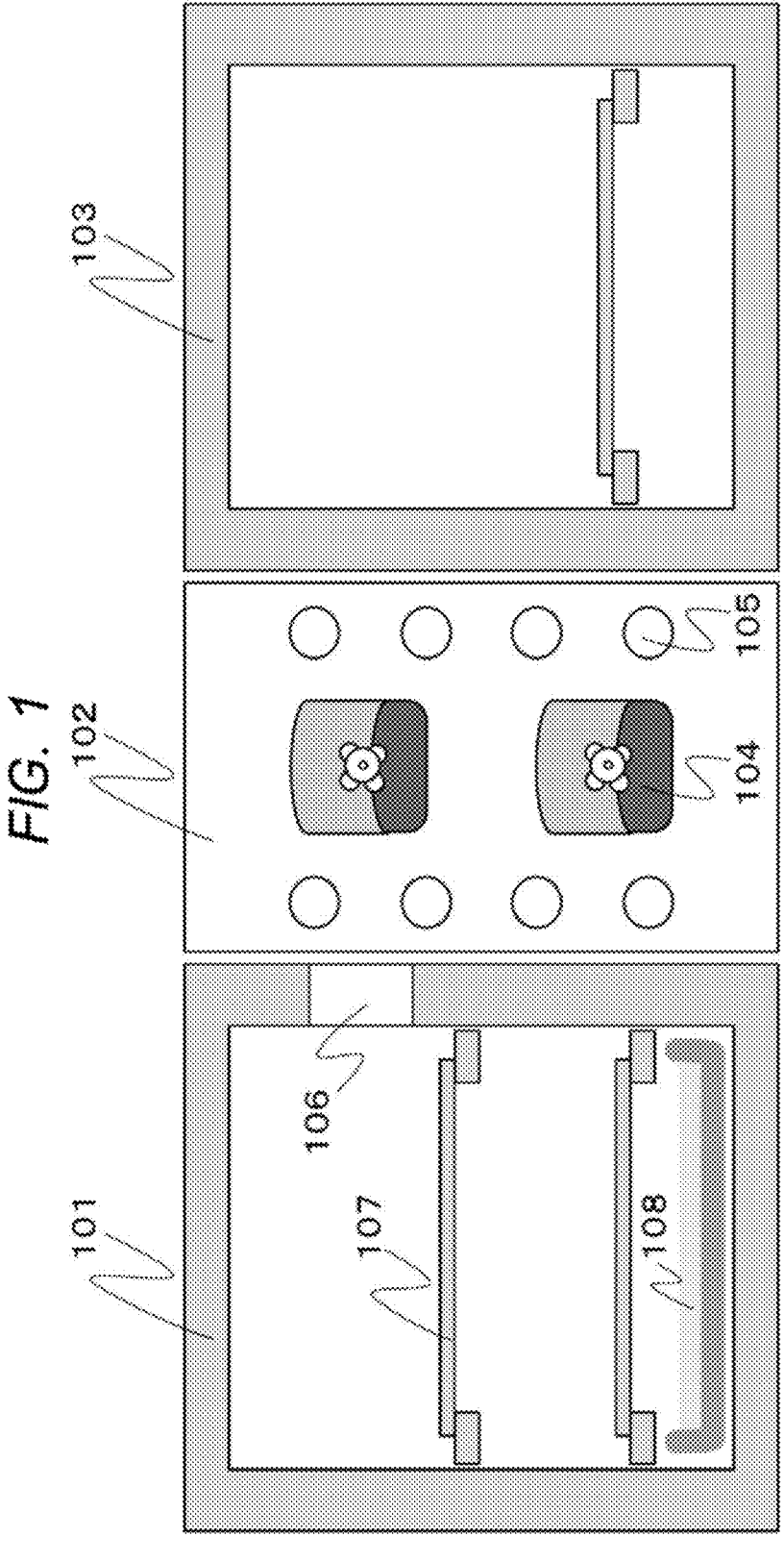
FIG. 1 is a diagram showing a configuration of a culture device according to an embodiment of the invention.

Hereinafter, preferred embodiments of the invention will be described in detail with reference to the accompanying drawings, but the invention is not necessarily limited thereto. The object, features, advantages, and ideas of the invention are apparent to those skilled in the art based on the present specification, and those skilled in the art can easily reproduce the invention based on the present specification. The embodiments and specific examples of the invention described below are preferred embodiments of the invention, are presented for purposes of illustration or description, and are not intended to limit the invention thereto. It is apparent to those skilled in the art that various changes and modifications can be made based on the description of the present specification within the spirit and scope of the invention disclosed herein.

A cell culture system of the invention includes an information processing device and an automatic culture device.

The automatic culture device includes a plurality of types of closed system flow paths possible to be installed and removed, and a plurality of culture devices. The information processing device includes: an input device configured to receive, as an input, at least one piece of data selected from a group consisting of data of an identifier of a patient, data related to a transplantation method, data related to a type of cell, data related to the required number of cells, and data related to a treatment plan; an arithmetic device configured to specify, based on the input data, from options of cell culture methods, the culture devices, and the closed system flow paths, a cell culture method, a culture device, and a closed system flow path for use; and an output device configured to output a number of the closed system flow path for use and a number of the culture device for use.

The closed system flow paths to be used for culture each includes a closed system culture container, a culture medium container, a culture supernatant container, and the like. According to a cell culture method corresponding to a type of cell to be cultured, a type of cell after culture, morphology of a regenerated tissue, and the like, it is possible to use various closed system flow paths having the closed system culture container and the like of different types, numbers, and the like. That is, in one automatic culture device, it is possible to execute culture using a plurality of types of closed system flow paths for which the cell culture method is different.

The information processing device includes the input device, the arithmetic device, and the output device. In order to use a plurality of types of closed system flow paths for a plurality of culture devices and perform a cell culture method according to each closed system flow path, a program for operating the plurality of culture devices is used in the information processing device. The program includes an electronic tag capable of associating each culture device and each closed system flow path with the cell culture method. The arithmetic device determines a cell culture method, a culture device, and a closed system flow path to be used based on at least one piece of the data selected from the group consisting of the data of the identifier of the patient, the data related to the transplantation method, the data related to the type of cell, the data related to the required number of cells, and the data related to the treatment plan received by the input device. The output device outputs a work procedure manual corresponding to the cell culture method to be used.

In this manner, cells are cultured by automatically selecting a culture device and a closed system flow path to be used for culture from the plurality of culture devices and the plurality of types of closed system flow paths, and thus it is possible to realize improvement of the integration property and reduction of the manufacturing cost of the cell culture system.

Hereinafter, embodiments of the cell culture system that automatically performs culture using a closed system flow path will be specifically described with reference to the drawings, but the cell culture system of the invention is not limited to the following embodiments, and can be measured in various ways by those skilled in the art.

Embodiment I

In the present Embodiment I, a cell culture system that automatically performs culture using a closed system flow path will be described with reference to FIGS. 1 and 2.

Each culture device includes an incubator 101 that is a space for culturing cells at a culture temperature of 37° C., a flow path mechanism portion 102 having a fluid supplying function, and a refrigeration portion 103 (FIG. 1). The flow path mechanism portion 102 includes a pump 104 and a solenoid valve 105. The refrigeration portion 103 stores a culture medium container containing a culture medium therein and a culture supernatant container for collecting a culture supernatant. Examples of shapes of these containers may include a bottle and a bag.

Figure 2:
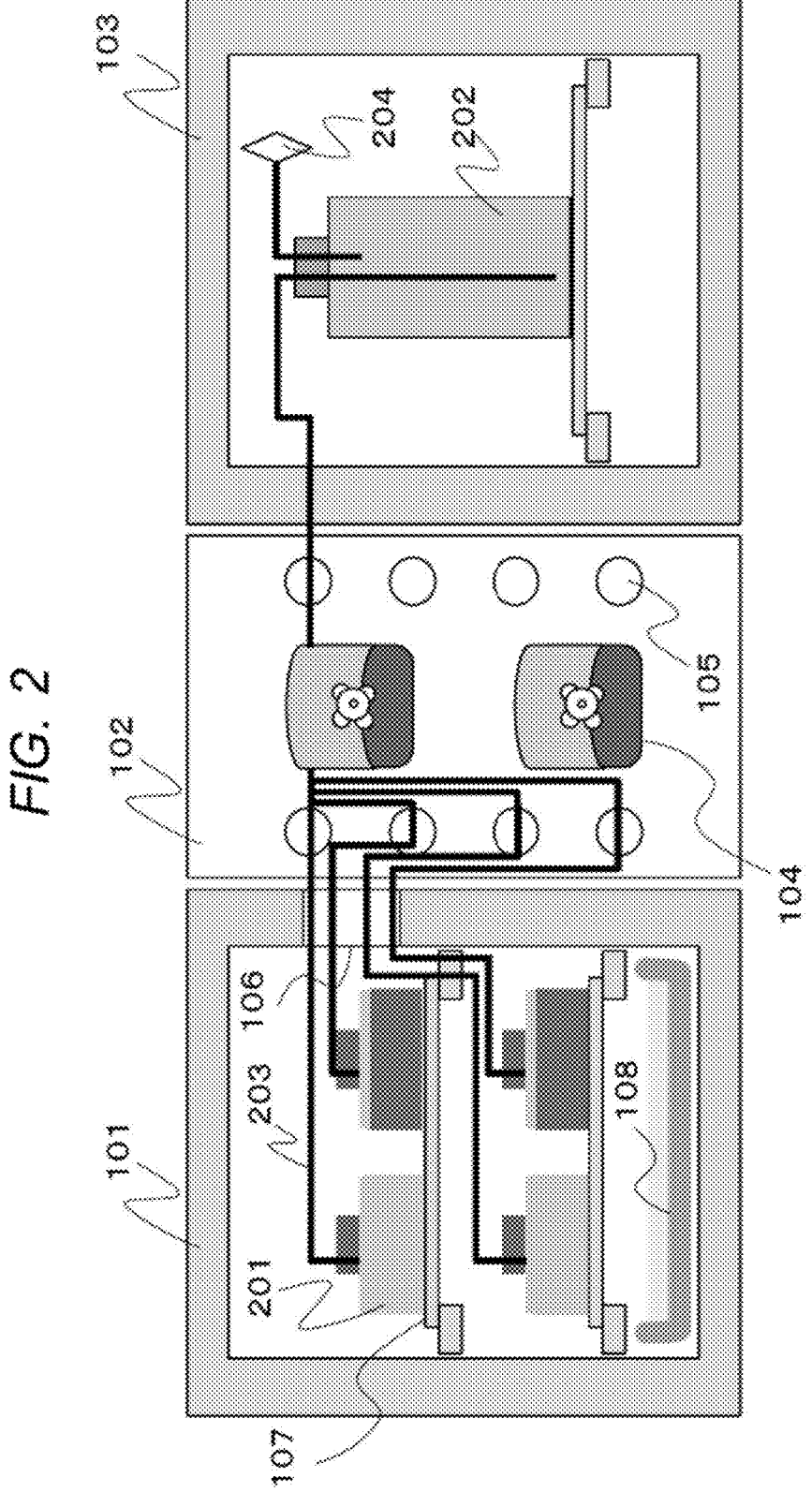
FIG. 2 is a diagram showing a state where a closed system flow path is installed in the culture device according to the embodiment of the invention.

FIG. 2 shows a state where the closed system flow path is installed inside the culture device of FIG. 1. A closed system culture container 201 for culturing cells is installed inside the incubator 101. The number of the closed system culture container 201 may be one or more. The closed system culture container 201 is constantly connected to a culture medium container 202, the culture supernatant container, and the like in the refrigeration portion 103 via a flow path tube 203. Since the flow path tube 203 is passed between the inside and the outside of the incubator 101, a cutout portion 106 serving as a space through which the flow path tube 203 passes is provided in the incubator 101. The cutout portion 106 may be provided either on a door or on a main body of the incubator 101. The cutout portion 106 has airtightness such that the inside of the incubator 101 can be maintained at an appropriate temperature, $CO_2$ concentration, and humidity in a state where the flow path tube 203 is installed. For example, the flow path tube 203 is made of a plastic material, and may be squashed to fill a gap of the cutout portion 106. In the cutout portion 106 through which the flow path tube 203 is passed, for example, the gap may be filled with a plastic jig. In a case where the flow path tube 203 is not installed, the gap of the cutout portion 106 may also be filled with the plastic jig fitted into the gap of the cutout portion 106. Accordingly, when being decontaminated by a decontamination gas such as hydrogen peroxide, the inside of the incubator 101 can be sealed even when the flow path tube 203 is not installed.

Next, an embodiment of the closed system flow path will be described with reference to FIGS. 3A to 3D. In the present embodiment, four types of closed system flow paths can be used in one automatic culture device, but the type and number of the closed system flow path are not limited thereto, and a closed system flow path in which the configuration is partially changed can also be used. Depending on the type of the closed system flow path, an implementable cell culture method varies, and a culture protocol used for the culture also varies.

Figure 3:
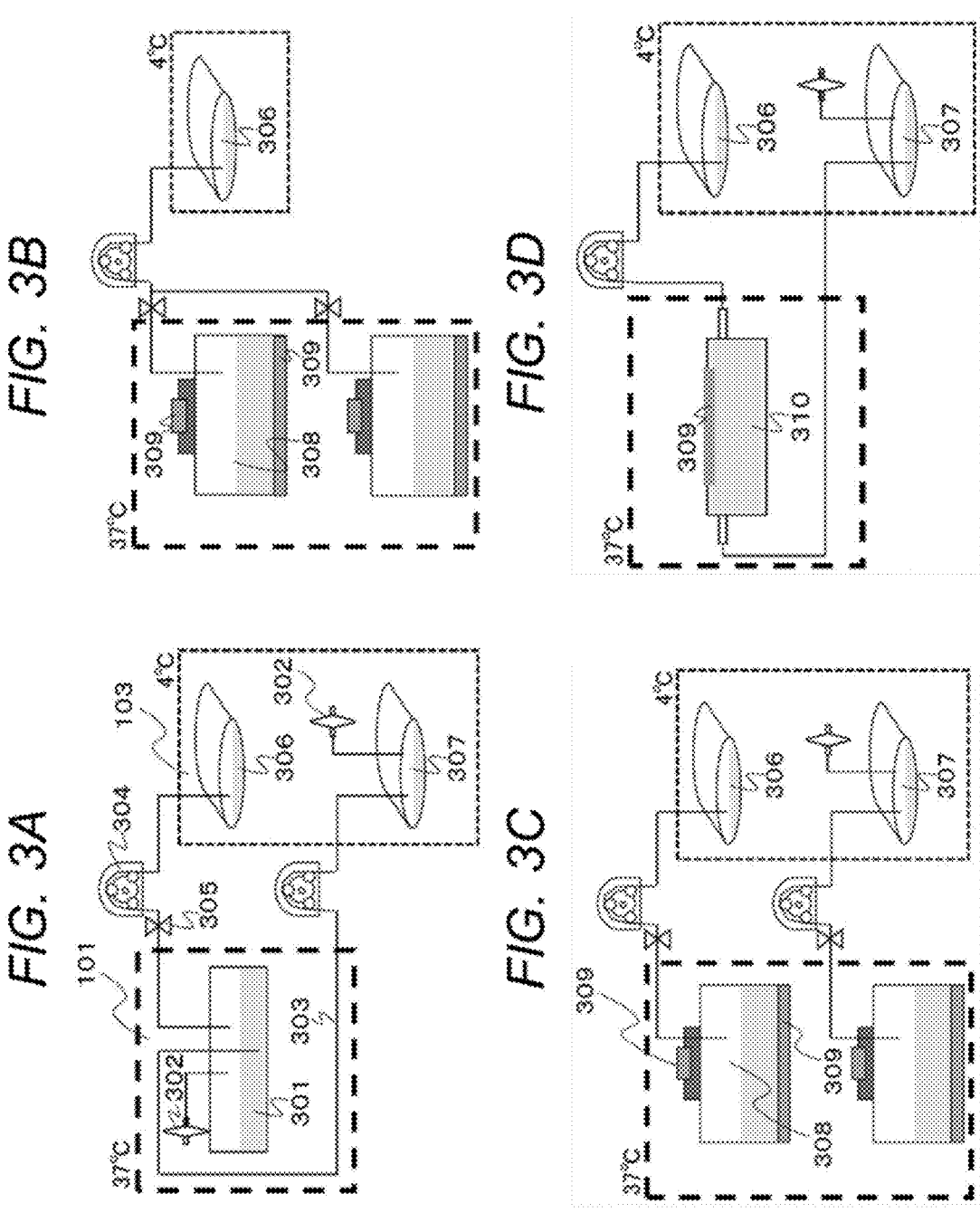
FIG. 3A is a diagram showing a type of closed system flow path installed in the culture device according to the embodiment of the invention.
FIG. 3B is a diagram showing another type of closed system flow path installed in the culture device according to the embodiment of the invention.
FIG. 3C is a diagram showing another type of closed system flow path installed in the culture device according to the embodiment of the invention.
FIG. 3D is a diagram showing another type of closed system flow path installed in the culture device according to the embodiment of the invention.

FIG. 3A shows, as an example, a flow path that enables adhesion culture of stem cells such as iPS cells and mesenchymal stem cells. In this configuration, both discharge of a culture supernatant already used for the culture and supply of a fresh culture medium can be performed in culture medium exchange. By adjusting a height of a pipe on a discharge side in a closed system culture container 301, the culture medium exchange can also be performed at any ratio. The incubator 101 is provided with an external filter-installed closed system culture container 301. The external filter-installed closed system culture container 301 includes a filter 302 for performing gas exchange between a gas phase in the incubator 101 and a gas phase in the external filter-installed closed system culture container 301. The refrigeration portion 103 is provided with a culture medium container 306 containing a fresh culture medium and a culture supernatant container 307. All components are constantly connected by a flow path tube 303. In the flow path tube 303, a driving force for supplying the culture medium or the like is applied by a pump 304 from the outside, a supplying direction at the time of supplying the culture medium or the like is selected via a solenoid valve 305, and thus the culture medium or the like is supplied by the pump 304 and the solenoid valve 305. During the culture, the solenoid valve 305 is closed. Although the external filter-installed closed system culture container 301 is used, a gas permeable membrane-installed closed system culture container 308 used in FIG. 3B may be used. As the culture protocol, the culture may be performed in which only supply of a fresh culture medium is performed, and the culture supernatant container 307 is not used.

FIG. 3B shows, as an example, a flow path that enables suspension culture of T cells. As the culture protocol, only supply of a culture medium is performed. A common culture medium container 306 is provided for two closed system culture containers 308. The gas permeable membrane-installed closed system culture containers 308 are installed in the incubator 101. The gas permeable membrane-installed closed system culture containers 308 each includes gas permeable membranes 309 for performing gas exchange between the gas phase in the incubator 101 and a gas phase in the gas permeable membrane-installed closed system culture container 308. The culture medium container 306 containing the fresh culture medium is installed in the refrigeration portion 103. At the time of supplying, the supplying direction is determined via two solenoid valves 305. The solenoid valve 305, for the gas permeable membrane-installed closed system culture container 308 to which a fluid is to be supplied, is opened, and the solenoid valve 305, for the gas permeable membrane-installed closed system culture container 308 to which the fluid is not to be supplied, is closed. During the culture, the solenoid valves 305 are closed. In FIG. 3B, the gas permeable membrane-installed closed system culture containers 308 each includes the gas permeable membranes 309 at two positions of a lid and a lower portion, but may include the gas permeable membrane at one of the two positions. Although the gas permeable membrane-installed closed system culture containers 308 are used, the external filter-installed closed system culture container 301 used in FIG. 3A may be used.

FIG. 3C shows, as an example, a flow path that enables suspension adhesion culture of T cells. As the culture protocol, only supply of a culture medium is performed. Each of the two closed system culture containers 308 includes the culture medium container 306 containing a fresh culture medium. That is, two closed system flow paths are used. In the drawing, the gas permeable membrane-installed closed system culture containers 308 each includes the gas permeable membranes 309 at two positions of the lid and the lower portion, but may include the gas permeable membrane at one of the two positions. Although the gas permeable membrane-installed closed system culture containers 308 are used, the external filter-installed closed system culture container 301 used in FIG. 3A may be used.

FIG. 3D shows, for example, a flow path that enables the adhesion culture of stem cells such as iPS cells and mesenchymal stem cells, and the suspension culture of T cells. As the culture protocol, perfusion culture is performed in which a fresh culture medium is supplied and at the same time a waste culture medium is discharged while maintaining a constant fluid amount. The incubator 101 is provided with a closed system culture container 310 for perfusion culture. The closed system culture container 310 for perfusion culture includes the gas permeable membrane 309 for performing gas exchange between the gas phase in the incubator 101 and a gas phase in the closed system culture container 310 for perfusion culture. The refrigeration portion 103 is provided with the culture medium container 306 containing the fresh culture medium and the culture supernatant container 307. In the drawing, the gas permeable membrane-installed closed system culture container 308 includes the gas permeable membrane 309 at one position of an upper portion, but may include the gas permeable membrane at the lower portion or at both the upper portion and the lower portion.

Next, a case where culture devices are used in a stacked state will be described with reference to FIGS. 4, 5, 6A and 6B.

Figure 4:
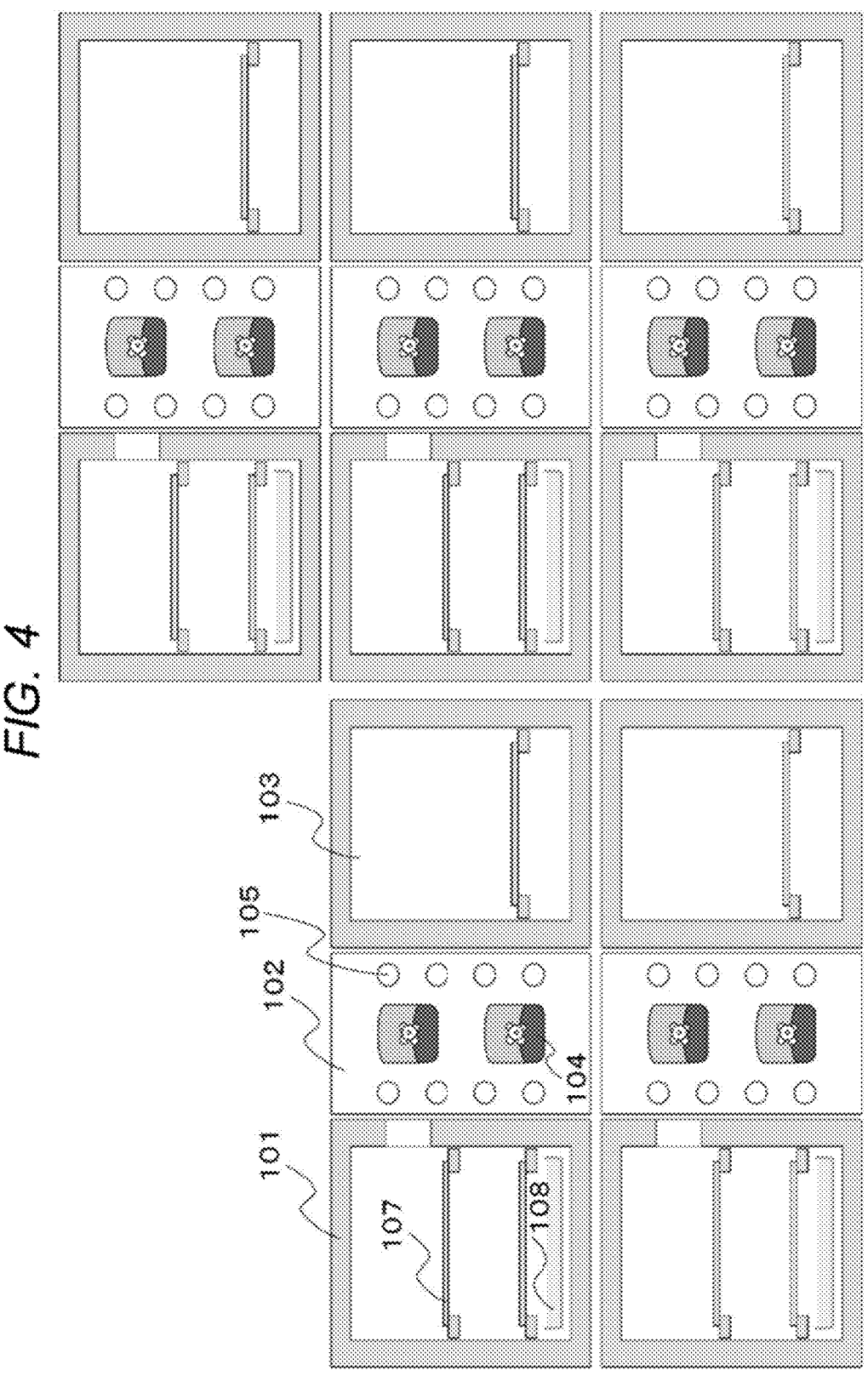
FIG. 4 is a diagram showing a configuration in which a plurality of culture devices are stacked according to the embodiment of the invention.
Figure 5:
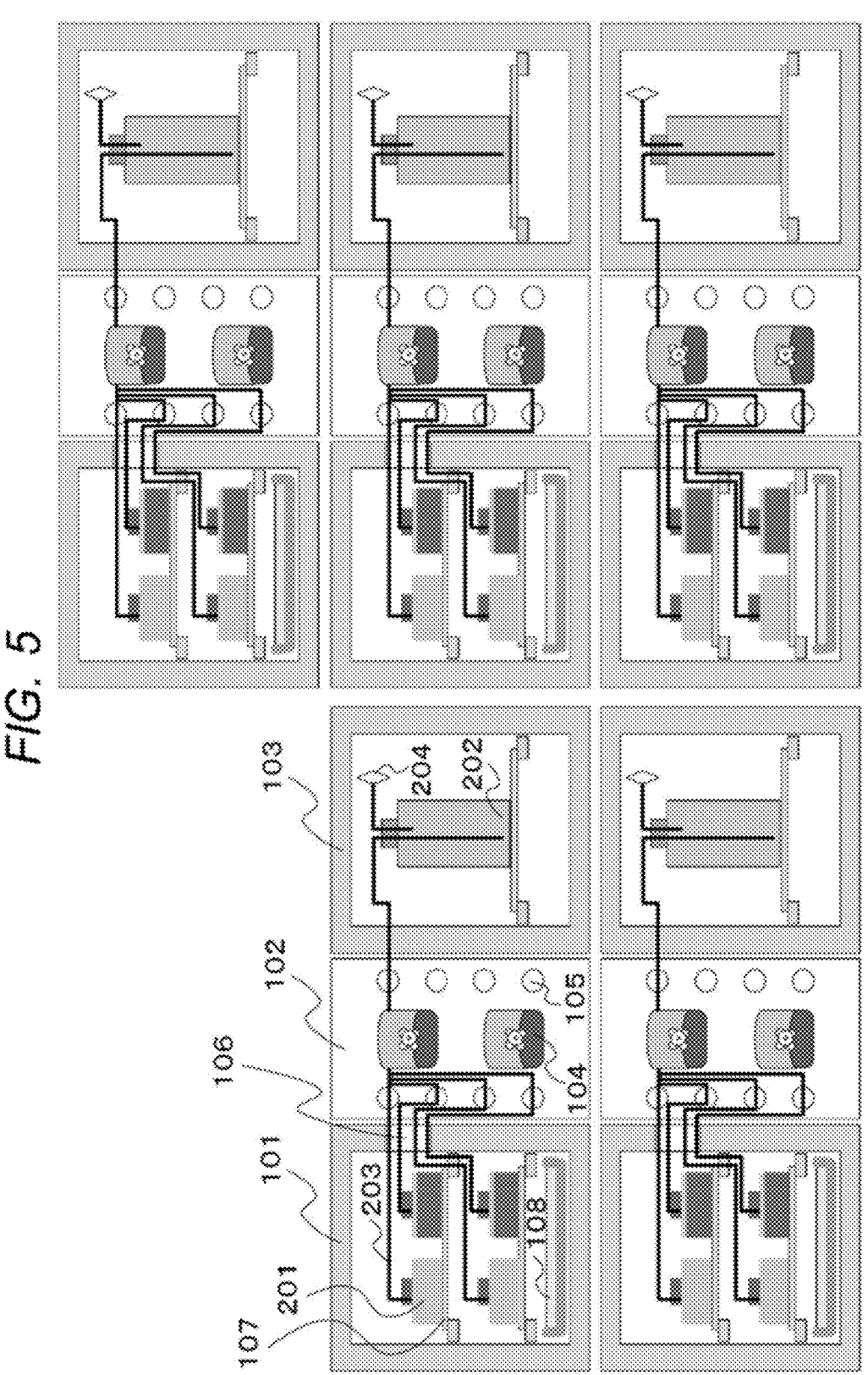
FIG. 5 is a diagram showing a state where, in the configuration in which the plurality of culture devices are stacked, a closed system flow path is installed in each culture device according to the embodiment of the invention.
Figures 6A, 6B:
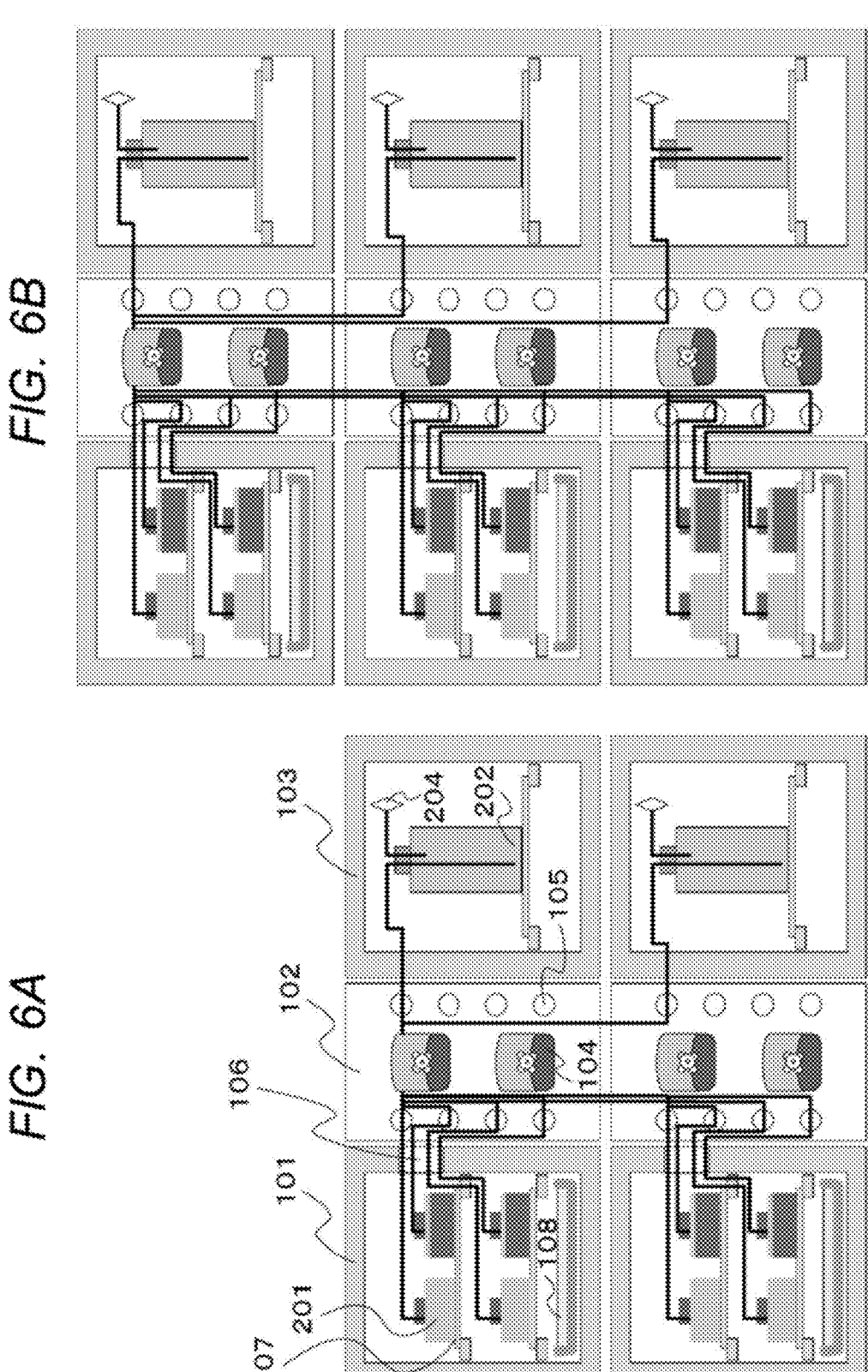
FIG. 6A is a diagram showing a state where, in a configuration in which a plurality of closed system automatic culture devices are stacked, one closed system flow path is installed for each of two culture devices according to the embodiment of the invention.
FIG. 6B is a diagram showing a state where, in a configuration in which a plurality of closed system automatic culture devices are stacked, one closed system flow path is installed for each of three culture devices according to the embodiment of the invention.

FIG. 4 shows, as an example, a state where two culture devices are stacked and a state where three culture devices are stacked. The number of culture devices to be stacked may be selected by a user according to a purpose or the like. FIG. 5 shows a case where culture is performed by one closed system flow path using one culture device. FIG. 6A shows a case where culture is performed by one closed system flow path using two culture devices. FIG. 6B shows a case where culture is performed by one closed system flow path using three culture devices. Although not shown here, the culture may be performed by one closed system flow path using four or more culture devices. As described above, in the automatic culture device of the present disclosure, a plurality of culture devices can be connected by one closed system flow path to perform the culture. Accordingly, it is possible to perform the culture for any number of culture containers and to manufacture a large amount of cells.

The closed system flow path includes closed system culture containers 201, culture medium containers, and culture supernatant containers corresponding to the number of culture devices. By opening and closing the solenoid valve 105, the supplying direction is switched to the culture container to which a fluid is to be supplied, and then the pump 104 is operated to supply the fluid to each culture container. The culture medium container is installed in each refrigerator. By opening and closing the solenoid valve 105, the supplying direction is switched to the culture medium container to which the fluid is to be supplied, and then the pump 104 is operated to supply the fluid from the culture medium container. When the culture is performed for a long period of time, since the service life of the culture medium is limited, a fresh culture medium may be installed using an aseptic connection portion. Since a large amount of culture medium is required for the culture, the culture medium may be separately provided in each refrigerator.

Next, another embodiment of the automatic culture device in which culture devices are used in a stacked state will be described with reference to FIGS. 7A to 7B. FIGS. 7A to 7B show automatic culture devices used in a state where two culture devices are stacked and in a state where three culture devices are stacked. A culture protocol that can be implemented also varies depending on the type of the closed system flow path. Therefore, the user can select the closed system flow path and select a culture method according to the selected closed system flow path.

FIGS. 7A and 7B are examples of automatic culture devices for culturing stem cells such as iPS cells and mesenchymal stem cells. FIG. 7A shows an automatic culture device in which two culture devices are used in a stacked state. FIG. 7B shows an automatic culture device in which three culture devices are used in a stacked state. As the culture protocol, both discharge of a culture supernatant already used for the culture and supply of a fresh medium can be performed in the culture medium exchange. By adjusting a height of a pipe on a discharge side in the closed system culture container 301, the culture medium exchange can also be performed at any ratio. The external filter-installed closed system culture container 301 is installed in the incubator 101. The culture medium container 306 is installed in the refrigeration portion 103. In FIG. 7A, two culture medium containers 306 and two culture supernatant containers are installed, but the number of the culture medium container 306 may be one or three depending on a required amount of the culture medium. The same applies to the culture supernatant container. Although the external filter-installed closed system culture container 301 is used, the gas permeable membrane-installed closed system culture container 308 may be used. As the culture protocol, the culture may be performed in which only the supply of the fresh culture medium is performed, and the culture supernatant container is not used. The same applies to the automatic culture device of FIG. 7B. FIGS. 7C and 7D show examples of flow paths for performing the suspension culture of T cells. FIG. 7C shows an automatic culture device in which two culture devices are used in a stacked state. FIG. 7D shows an automatic culture device in which three culture devices are used in a stacked state. As the culture protocol, only supply of a culture medium is performed. The gas permeable membrane-installed closed system culture containers 308 are installed in the incubator 101. The culture medium container 306 is installed in the refrigeration portion 103. In FIG. 7C, two culture medium containers 306 are installed, but the number of the culture medium container 306 may be one or three depending on a required amount of the culture medium. Although the gas permeable membrane-installed closed system culture container 308 is used, the external filter-installed closed system culture container 301 may be used. The same applies to the automatic culture device of FIG. 7D.

When culturing cells of a large number of patients, it is preferable to install culture devices in an integrated state in a cell preparation chamber of one room. In each culture device, cells of different patients can be cultured by respective culture programs thereof. The culture programs vary depending on the type of cell to be cultured, and a schedule of the culture programs varies depending on a treatment schedule such as transplantation, which is different for each patient. In each closed system flow path to be used, the type and number of culture containers vary depending on the type and transplantation form of cells to be cultured. Therefore, it is necessary to appropriately select a culture program, a closed system flow path, and a culture device to be used for each patient from a plurality of culture programs, closed system flow paths, and culture devices.

Figure 9:
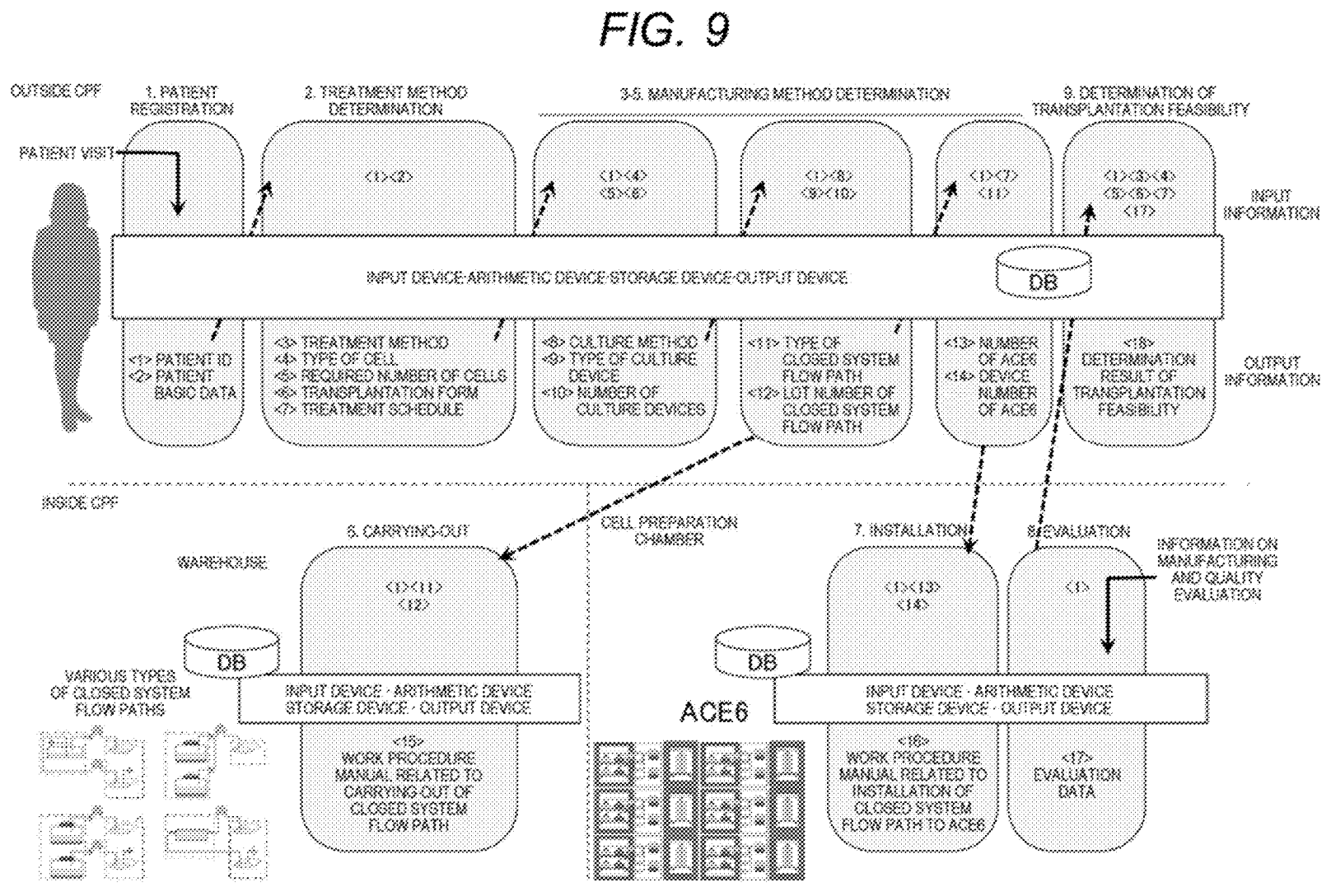

Culture information related to a plurality of culture devices and a plurality of closed system flow paths to be used for the culture, which is handled by a culture program provided in the information processing device, will be described with reference to FIG. 8. The table in FIG. 8 shows generation and acquisition of culture information generated in each step. FIG. 9 shows a flow of the culture information related to the plurality of culture devices and the plurality of closed system flow paths used for the culture, and a relationship between the culture information and a culture program handling the culture information. The information processing device is equivalent to a normal computer including: a processing unit consisting of a central processing unit (CPU); a storage unit; a display device; and an input and output unit consisting of a keyboard. The input device and the arithmetic device are provided in the CPU, and a device for displaying corresponds to the display device.

From the time when a patient visits the hospital, information on cells to be manufactured is generated in accordance with determination of a treatment method. The output device is caused to output a work procedure protocol related to removal of a closed system flow path to be used and specification of a selected culture device, and to display the work procedure protocol on the device for displaying. When each item is determined and input to the input device, the arithmetic device limits options in the subsequent selections according to determination content of the item, the output device outputs the options to the device for displaying, and the device for displaying displays the options. For example, when the type of cells to be manufactured is determined and input to the input device, the arithmetic device limits a type of a culture container possible to be used for the culture to a type corresponding to the type of cells, the output device outputs the options to the device for displaying, and the device for displaying displays the options. When the type, the number, and the transplantation form of the cells to be manufactured are determined and input to the input device, the arithmetic device limits the manufacturing method in accordance with conditions thereof.

When determining the manufacturing method, first, a type of the closed system flow path to be used is determined and input to the input device. The type of the closed system flow path is determined according to the type and number of culture containers to be used. Next, the culture device to be used is determined and input to the input device. A culture period differs depending on the cells to be manufactured, that is, an operation period of the automatic culture device also differs. A culture schedule changes for each patient. The manufacturing cost is reduced when an operation rate of the device is increased and cells of as many patients as possible are manufactured, and therefore a culture device to be used may be selected such that the operation rate is as high as possible. When carrying out the closed system flow path to be used from a warehouse, a lot number of the closed system flow path to be carried out is displayed in the work procedure protocol on the device for displaying. An electronic tag or a two-dimensional barcode having information of the lot number is attached to the closed system flow path in advance, and it is confirmed that the lot number displayed in the work procedure manual matches the information of the electronic tag or the two-dimensional barcode of the selected closed system flow path. When installing the closed system flow path to be used in the culture device, a device number of the culture device to be used is displayed in the work procedure protocol on the device for displaying. An electronic tag or a two-dimensional barcode having information of the device number is attached to the culture device in advance, and it is confirmed that the lot number displayed in the work procedure manual matches the information of the electronic tag or the two-dimensional barcode of the selected culture device. According to the above-mentioned method, an erroneous selection is avoided in the selection of the closed system flow path and culture device to be used. After the manufacturing, a quality evaluation result is used to determine whether to perform a treatment using the manufactured cells.

Figures 10A, 10B, 10C, 10D:
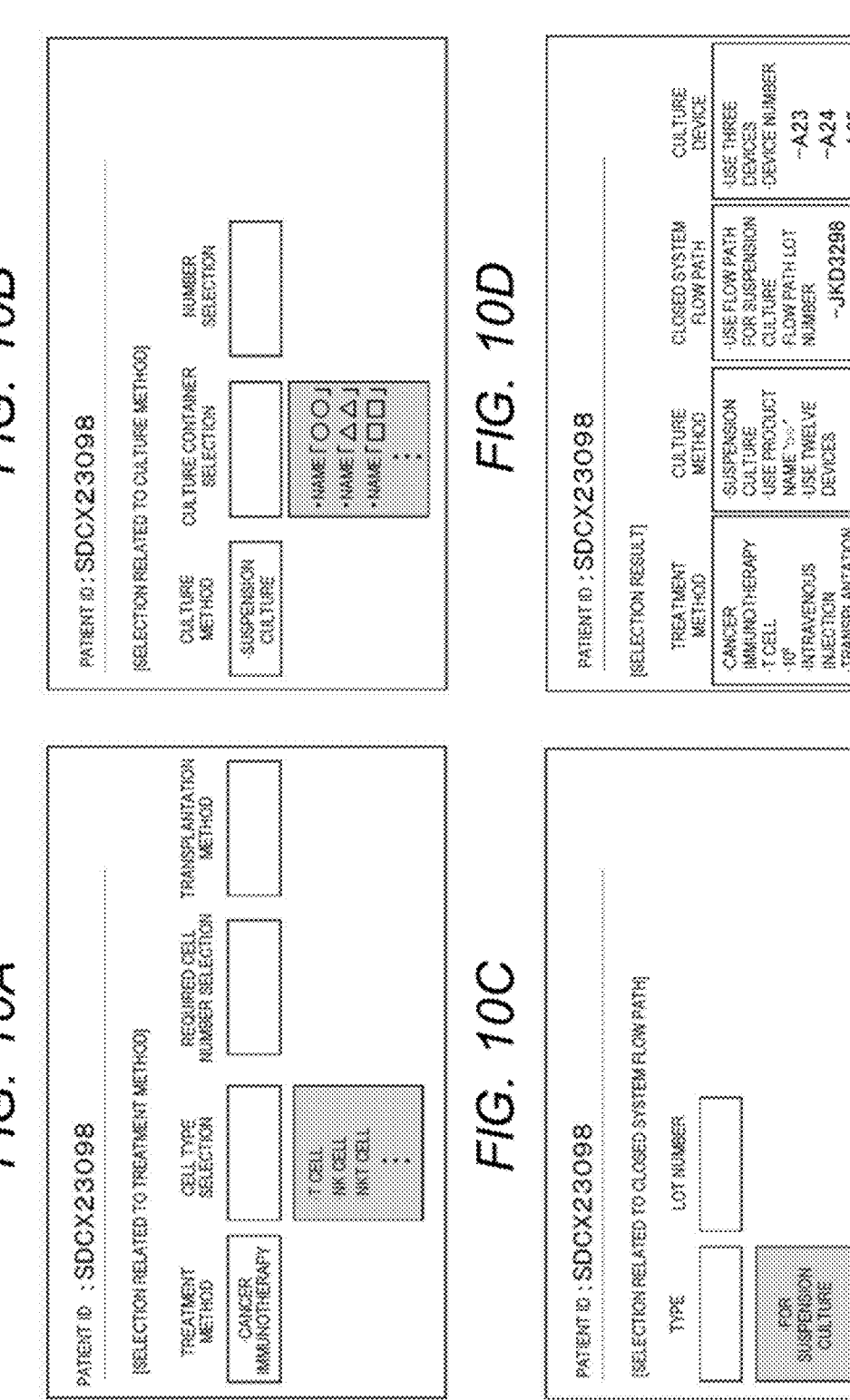
FIG. 10A is a diagram showing a screen example of a culture program according to the embodiment of the invention.
FIG. 10B is a diagram showing another screen example of the culture program according to the embodiment of the invention.
FIG. 10C is a diagram showing another screen example of the culture program according to the embodiment of the invention.
FIG. 10D is a diagram showing another screen example of the culture program according to the embodiment of the invention.

FIGS. 10A to 10B show examples of a display screen of the work procedure protocol driven by the culture program. FIG. 10A is a screen for selecting the type of cell in the selection related to the treatment method. Before the type of cell is selected, in this example, cancer immunotherapy is selected as the treatment method, and therefore, in the selection of the type of cell, only types of cells usable for the cancer immunotherapy are displayed as options, and the type of cell is selected from the options. Types of cells that are not used for the cancer immunotherapy are not displayed, thereby avoiding an erroneous selection. FIG. 10B shows a screen for selecting the type of culture container in the selection related to the culture method. Before the type of the culture container is selected, since a suspension cell is selected as the culture method, in the selection of the type of the culture container, only types of culture containers usable for the suspension cell are displayed as options, and the type of the culture container is selected from the options. A similar selection form is applied to FIG. 10C. FIG. 10D is a screen displaying all the selected information.

Figure 11:
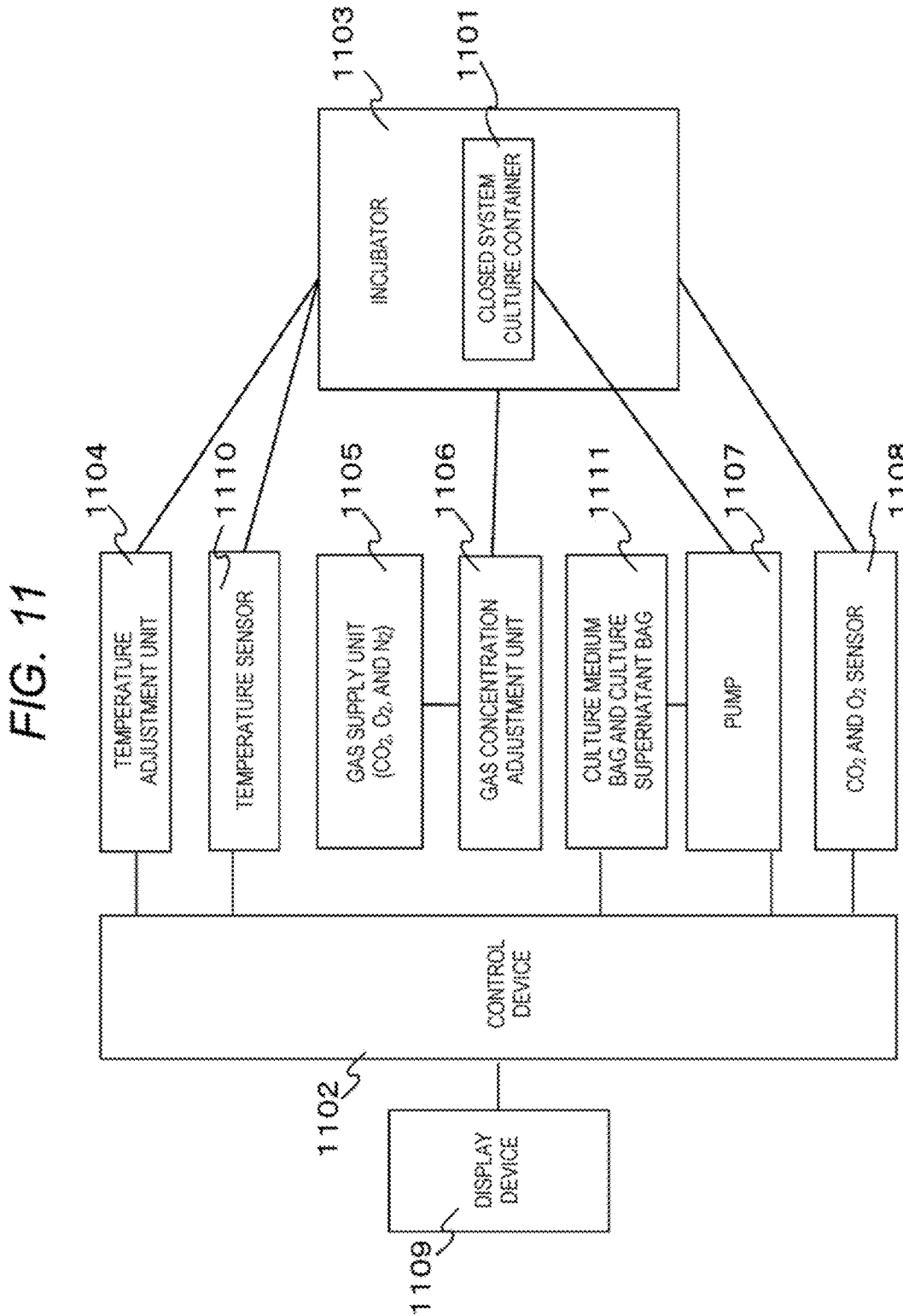
FIG. 11 is a diagram showing a control mechanism of an automatic culture device according to the embodiment of the invention.

FIG. 11 is a block diagram illustrating a functional configuration of an automatic culture device including a culture container 1101. The block diagram is an overall configuration diagram in which respective components controlled by a control device 1102 provided in the information processing device are connected to each other or to an incubator 1103. The incubator 1103 is provided with the above-described closed system culture container 1101. The control device 1102 is connected with: a temperature adjustment unit 1104 for controlling a temperature of the incubator 1103; a gas concentration adjustment unit 1106 that is provided with a gas supply unit 1105 and is used for controlling a gas concentration in the incubator 1103; a pump 1107 installed in a closed system flow path circuit for automatically supplying a culture medium in the closed system culture container 1101; and a $CO_2$ and $O_2$ sensor 1108. The control device 1102 is provided in the CPU of the normal computer. The control device 1102 causes various programs stored in the storage unit to operate on the CPU serving as the processing unit. Accordingly, a culture environment in the incubator 1103 is controlled through the temperature adjustment unit 1104, the gas supply unit 1105, the pump 1107, the $CO_2$ and $O_2$ sensor 1108, the gas concentration adjustment unit 1106, a temperature sensor 1110, a culture medium bag and culture supernatant bag 1111, and a predetermined culture process in the closed system culture container 1101 can be performed. Gas exchange in the closed system culture container 1101 is performed between the incubator 1103 and the closed system culture container 1101 using a gas permeable membrane installed in the closed system culture container 1101. The gas concentration adjustment unit 1106 may be directly connected to the closed system culture container 1101. The temperature adjustment unit 1104, the gas concentration adjustment unit 1106, and the $CO_2$ and $O_2$ sensor 1108 may be connected to the closed system culture container 1101. In the case of this configuration, a gas is directly supplied into the closed system culture container 1101.

Figure 12:
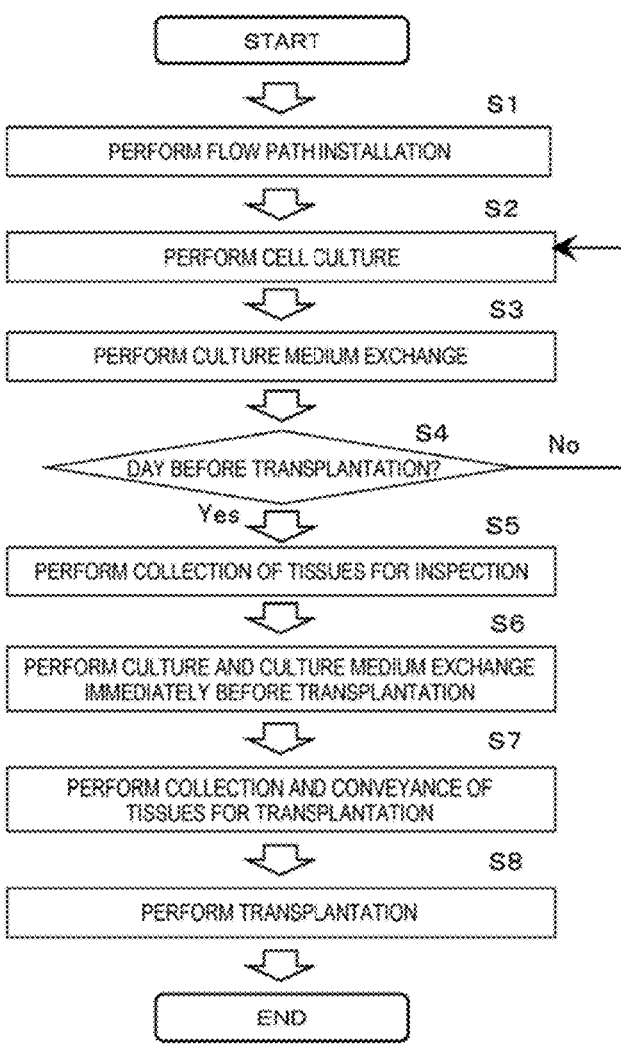
FIG. 12 is a flowchart showing a flow during operation of the closed system automatic culture device according to the embodiment of the invention.

A series of procedures for manufacturing a regenerated tissue using the automatic culture device having the above-mentioned functions are shown in FIG. 12.

Step S1: Flow Path Installation

The automatic culture device is started. As information of a plurality of culture devices to be used, device numbers and the like are recorded in the work procedure protocol. The electronic tag or the two-dimensional barcode is provided in each culture device in advance, and it is preferable to confirm in advance, by reading the electronic tag or the two-dimensional barcode by a barcode reader or the like, that the electronic tag or the two-dimensional barcode matches the information such as the device number recorded in the work procedure protocol. An operator presses a start switch of an operation unit in the control device and starts the automatic culture device. The inside of the device is made a clean environment by performing disinfection or sterilization in advance.

Subsequently, it is confirmed on an operation screen of a display of a control unit that the internal environment of the automatic culture device is appropriate. For example, it is confirmed that a temperature of the incubator is 37° C. These numerical values are not limiting, and for example, the temperature can be selected from a range of 0° C. to 45° C. An automatic culture schedule is determined in advance by the culture program, and information thereof is reflected to the automatic culture device. The automatic culture schedule also includes conditions such as dates and times when cell seeding, culture medium exchange, collection of culture supernatant, collection of tissues for inspection, collection of tissues for transplantation, and the like are performed, and the fluid amount.

A closed system flow path including a closed system culture container is installed in the culture device in advance. In addition, when the closed system flow path is carried out from the warehouse, it is confirmed in advance, by reading the electronic tag or the two-dimensional barcode provided in advance in the closed system flow path by the barcode reader or the like, that the electronic tag or the two-dimensional barcode matches the information such as the device number recorded in the work procedure protocol. The closed system flow path includes the closed system culture container, the culture medium container containing the fresh culture medium, the gas permeable membrane-installed closed system culture container for collecting a culture supernatant after culture, and the like, and a flow path tube connecting those. The configuration corresponds to the type of the selected closed system flow path. When performing cell seeding by manual work, cells are seeded in a safety cabinet in advance, and the closed system culture container containing a cell suspension is installed in the device. When performing the cell seeding automatically by the automatic culture device, a cell suspension prepared in advance at a predetermined concentration is put into a cell bottle in the safety cabinet, and a closed system culture container containing the cell suspension is installed in the device. After automatic culture is started, the automatic culture device performs the seeding by supplying the cell suspension from the cell bottle to each closed system culture container.

Step S2: Cell Culture

Cells are cultured for a predetermined period of time in a state where the closed system culture container is left to stand. During the culture, the temperature is maintained at 37° C. by the incubator. Air in the device is constantly agitated by a fan such that temperature distribution is uniform therein. In order to improve manufacturing safety, a particle counter or a viable bacteria-counting device may be attached to the device to monitor cleanliness. When a closed system culture container including a gas permeable membrane, a filter, or the like is used for the gas exchange, the gas phase in the incubator and the gas phase in the closed system culture container are subjected to the gas exchange via the gas permeable membrane, the filter, or the like. When a closed system culture container including an air supply flow path is used, the gas exchange is performed by directly supplying a predetermined gas into the closed system culture container. The gas exchange is performed several times or more per day during the culture period. As the gas to be supplied, for example, air containing $CO_2$ of a concentration of 5% is used. The gas is sent out from a gas cylinder while a flow rate is controlled by a gas flowmeter, and is supplied to each closed system culture container through a humidification bottle in order to saturate water vapor. Unnecessary gas after the supply of gas to the closed system culture container is discharged to the outside of the flow path through the filter. It is preferable to use a filter of, for example, 0.22 μm or more.

Step S3: Culture Medium Exchange

The culture medium exchange is performed once every several days during the culture period. The culture medium exchange may also be performed by a culture medium addition of only adding a fresh culture medium. A culture medium stored at 4° C. in a refrigerator is supplied to a preheating bottle and is preheated to 37° C. The temperature thereof may be raised to 37° C. while supplying the culture medium at a low fluid supplying rate. In the culture medium exchange, a waste culture medium is first discharged from the closed system culture container. After the discharge, a fresh culture medium is quickly supplied into the closed system culture container. The waste culture medium is finally discharged to the culture supernatant container. If necessary, the culture supernatant in the culture supernatant container is collected, and a growth state of the cells is evaluated by culture medium component analysis. The culture medium may be exchanged by pushing out the fresh culture medium in a state where the waste culture medium is contained.

Step S4: Confirmation of Whether Date is the Day Before Scheduled Transplantation Date It is confirmed whether the date is the day before the scheduled transplantation date, and if the date is not the day before the scheduled transplantation date, the process returns to step S2 to continue the culture. If the date is the day before the scheduled transplantation date, the process proceeds to a next step.

Step S5: Collection of Tissues for Inspection

When a plurality of closed system culture containers are simultaneously used in the culture, a part of the closed system culture containers may be collected for inspection. A door of the culture device is opened, the flow path tubes of the closed system culture containers for inspection are aseptically cut by means such as thermal welding, and the closed system culture containers are taken out. The removed closed system culture containers are conveyed to the outside of the safety cabinet or the CPF, and the inspection is promptly performed. For example, the number of cells, a survival rate, expression of a specific protein, and the like of a biological sample are evaluated.

Step S6: Culture and Culture Medium Exchange Immediately Before Transplantation

The culture is performed by the same operations as in step S3. Immediately before step S7 is performed, the culture medium exchange is performed by the same operations as in step S4.

Step S7: Collection and Conveyance of Tissues for Transplantation

As a result of the evaluation in step S5, when it is determined that the biological sample is in a state suitable for transplantation, the biological sample is collected and used for a regenerative medical treatment. Similar to step S5, the closed system culture containers are aseptically separated from the closed system flow paths and taken out from the incubator. If necessary, processing of carrying into the safety cabinet is performed.

The closed system culture containers are stored in a transport container for a short distance or a long distance in a shipping room. By using a heat storage material, an airtight container, packaging, and the like, an influence of temperature, pressure, impact, or the like is minimized over an entire process during transportation. In this state, the transport container is carried to the outside of the CPF and is transported to an operating room by means of a vehicle, a railroad, an aircraft, a manual transport, or the like as necessary. Before a treatment in the operating room, cell observation using a microscope is performed as an acceptance inspection as necessary. In a case of a short distance transportation, it is assumed that the state is hardly changed from a state immediately before the transportation, and therefore, it is not necessary to perform the cell observation according to the determination of the operator.

Step S8: Transplantation

After arriving at the operating room, the regenerated tissue is taken out from the closed system culture container. At the time of opening, since organisms such as bacteria and particles may be attached to the outside of the closed system culture container, the closed system culture container is aseptically opened so as to maintain cleanliness of the inside thereof.

Finally, the closed system flow path used for the culture is removed. Subsequently, the inside of the device is subjected to a decontamination using a decontamination gas or a wiping disinfection using ethanol or the like by an appropriate operation to obtain a clean state. Various types of software of the automatic culture device are ended, and the operation of the automatic culture device is ended.

According to a preferred embodiment of the automatic culture device including the closed system culture container configured as described above, by using a culture program for operating the plurality of culture devices using a highly versatile closed system flow path, the integration property of the culture devices can be improved, and as a result, the manufacturing cost can be reduced.

Embodiment II

Figure 13:
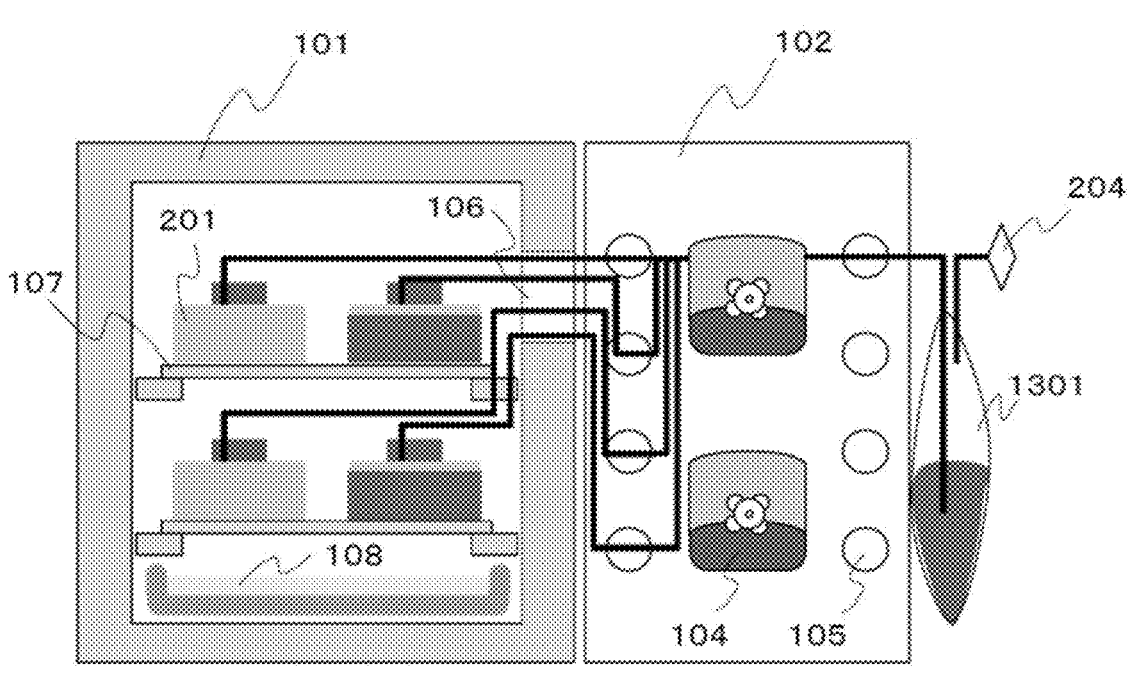
FIG. 13 is a diagram showing a configuration of a culture device in which a refrigerator is not provided and a culture medium container is installed on a side surface of the device at room temperature according to another embodiment of the invention.

An implementation method using an automatic culture device having a configuration different from that of Example 1 will be described with reference to FIG. 13.

In the present embodiment, the refrigeration portion provided in Embodiment I is not provided. The culture medium container and the culture supernatant container are installed on the side surface of the device at room temperature. In FIG. 13, a culture medium container 1301 is installed.

The closed system flow path can be installed in the same manner as in Embodiment I. The culture device can be integrated by a method such as stacking. Cells can be cultured by using one closed system flow path for a plurality of culture devices. As a result, a large amount of cells can be cultured. Since a plurality of culture devices are operated, the culture program shown in Example 1 can be used.

Embodiment III

Figure 14:
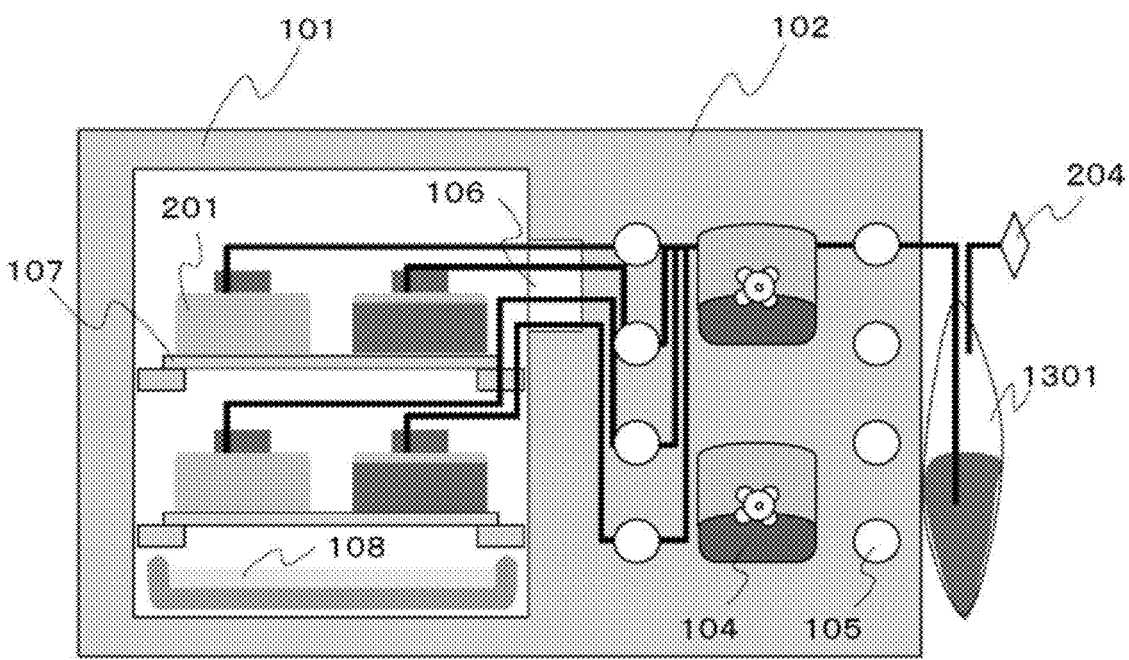
FIG. 14 is a diagram showing a configuration of a culture device in which a refrigerator and a flow path mechanism portion are not provided and a culture medium container is installed on a side surface of the device at room temperature according to another embodiment of the invention.

An implementation method using an automatic culture device having a configuration different from that of Embodiment I will be described with reference to FIG. 14.

In the present example, the refrigeration portion provided in Embodiment I is not provided. The flow path mechanism portion 102 in Embodiment I is integrated with the incubator 101. The culture medium container, the culture supernatant container, and the like are installed on the side surface of the device at room temperature. In FIG. 14, a culture medium container 1401 is installed.

It is possible to install a closed system flow path in the same manner as in Embodiment I. The culture device can be integrated by a method such as stacking. Cells can be cultured by using one closed system flow path for a plurality of culture devices. As a result, a large amount of cells can be cultured. Since a plurality of culture devices are operated, the culture program shown in Embodiment I can be used.

What is claimed is:

1. A cell culture system for culturing cells of different patients, the cell culture system comprising:

a plurality of automatic culture devices respectively comprising culture containers;

a plurality of types of closed system flow paths configured to be installed and removed with respect to the plurality of automatic culture devices, wherein one from among the plurality of types of closed system flow paths is installed to connect the plurality of the automatic culture devices, wherein the plurality of automatic culture devices are connected by the one closed system flow path to perform cell culture; and an information processing device comprising at least one hardware processor configured to execute computer-readable instructions to:

receive, as an input, at least one piece of data comprising data of an identifier of a patient from among the different patients, data related to a transplantation method, data related to a type of cell of the patient, data related to a number of cells to culture, and data related to a treatment plan related to the patient;

select, based on the at least one piece of data as the input, a cell culture method among different cell culture methods, at least one automatic culture device among the plurality of automatic culture devices, and at least one type of a closed system flow path among the plurality of types of closed system flow paths; and output information associated with the selected at least one automatic culture device and the selected at least one type of a closed system flow path.

2. The cell culture system according to claim 1, wherein one or more types of the plurality of types of closed system flow paths includes a valve for opening and closing a flow path tube, a pump for supplying a fluid or gas in the flow path tube, a culture medium container for holding a fresh culture medium, and a culture supernatant container for holding a culture supernatant after culture.

3. The cell culture system according to claim 1, wherein the at least one hardware processor is configured to output a work procedure manual related to the selected at least one type of the closed system flow path.

4. The cell culture system according to claim 1, wherein the at least one hardware processor is configured to output a work procedure manual related to the selected culture device.

* * * * *